United States Patent
Lyons, Jr. et al.

(10) Patent No.: US 6,708,555 B1
(45) Date of Patent: Mar. 23, 2004

(54) DIELECTRIC WOOD MOISTURE METER

(76) Inventors: William F. Lyons, Jr., 2 Riffles La., Hudson, MA (US) 01749; Ronald Lessard, 5 King St., Barre, VT (US) 05641

(*) Notice: Subject to any disclaimer, the term of this patent is extended or adjusted under 35 U.S.C. 154(b) by 0 days.

(21) Appl. No.: 10/298,299

(22) Filed: Nov. 18, 2002

(51) Int. Cl.$^7$ ............................. G01N 5/02; G01R 27/04
(52) U.S. Cl. .......................................... 73/73; 324/640
(58) Field of Search ..................... 73/73–77; 324/640, 324/661

(56) References Cited

U.S. PATENT DOCUMENTS

| | | | | |
|---|---|---|---|---|
| 4,580,233 A | * | 4/1986 | Parker et al. ................... | 73/73 |
| 5,488,312 A | * | 1/1996 | Havener et al. ............. | 324/689 |
| 5,514,973 A | * | 5/1996 | Byler et al. ................. | 324/695 |
| 5,621,391 A | * | 4/1997 | Elseth ......................... | 340/604 |
| 6,340,892 B1 | * | 1/2002 | Rynhart et al. ............. | 324/640 |
| 2003/0062908 A1 | * | 4/2003 | Venter et al. ............... | 324/661 |
| 2003/0146767 A1 | * | 8/2003 | Steele et al. ................ | 324/640 |
| 2003/0169054 A1 | * | 9/2003 | Rynhart et al. ............. | 324/649 |

* cited by examiner

Primary Examiner—Edward Lefkowitz
Assistant Examiner—Takisha S Miller

(57) ABSTRACT

A wood moisture meter for measuring the moisture content of wood by monitoring the dielectric constant of the wood as a dependent variable of the amount of moisture in the wood. The sensor is a pair of parallel plates which, when encased in a plastic film, placed side by side in direct contact with the wood and in a snake-like pattern, will form the plates of a capacitor in the which the dielectric material is the wood itself. The capacitor is used in a circuit, the input for which is a nominal voltage of 5V, the output of which is a pulse of a length directly proportional to the varying dielectric constant of the wood as the wood dries in a wood drying kiln. The pulse length is correlated with the appropriate wood moisture content and provided to the operator of the kiln.

6 Claims, 5 Drawing Sheets

| | |
|---|---|
| $R_1$ = 68 KΩ | $C_1$ = 0.001 μF |
| $R_2$ = 680 KΩ | $C_2$ = 0.003 μF ‖ 0.01 μF |
| $R_3$ = 1 KΩ | $C_3$ = 0.01 μF |
| $R_4$ = 1.2 MΩ | $C_4$ = VARIABLE (WOOD) |

$MC_0$ = Equilibrium Moisture Content (Wood is Dry)

DIELECTRIC WOOD MOISTURE METER

BACKGROUND OF THE INVENTION

The present invention relates to a device for use in a wood drying kiln. More specifically, the present invention measures the moisture content at the surface of a sample of wood. The purpose of the invention is to determine the moisture content of the wood, which, when viewed in conjunction with other metrics, allows a manufacturer of lumber to determine if the lumber is adequately cured for use in wood products.

The wood drying industry, like most other industries, is progressively becoming more automated. Every industry is unique in the challenges it poses to automate the processes required for the manufacturing of products. This invention addresses one such unique automation challenge.

In order to dry wood correctly, certain parameters must be periodically monitored in a wood drying kiln. The parameters that must be monitored are humidity, temperature, and the subject of this invention—wood moisture content. The first two parameters have been automated in the past as a result of technological innovations in other fields. However, the measuring of wood moisture content has been more difficult to automate.

In the past, the measuring of wood moisture content has been a strictly manual task. In order to measure wood moisture content in a kiln, an employee would need to walk into an extremely hot and humid kiln. The employee would then obtain a wood representative sample of the drying lumber. The wood sample would then be weighed. The weight of the sample of wood would be compared to established charts based on the species of the tree and the size of the sample to extrapolate the moisture content of the sample.

Once the moisture content of the sample was extrapolated, the operator of the wood drying kiln would assume that all of the wood in the kiln of the same species contained the same moisture content as the representative sample. This process is fraught with potential areas for error and economic inefficiencies. As a result, the automation of this process using more accurate technological innovations is desirable.

The undesirable aspects of the manual measuring of wood moisture content are several. First, a human being is required to enter a very acrid wood drying kiln, thereby exposing the employee to potentially hazardous fumes, including tanic acid content from the evaporating wood resins. In addition, as human beings are fallible and subject to error, it is possible that the employee in the kiln, in a hurry to exit the uncomfortable and potentially hazardous environment, might make an error in measurement, thereby jeopardizing the quality or marketability of the final product.

Second, the manufacturer must sacrifice wood samples to be measured periodically for wood moisture content, which is economically inefficient. The samples used to measure the wood moisture content would necessarily be smaller that many of the other pieces of lumber in the kiln due to the limitations of using a scale to measure the sample's weight. The sample would need to be of a size and weight that could be easily manipulated by the employee conducting the measurements, thereby limiting its uses and sales potential once the drying process was concluded.

Lastly, the representative wood sample may not actually represent the wood moisture content of the entire batch of a particular species due to regional and individual variations in the lumber. This could result in some inaccuracies in the "measured" wood moisture content, causing wood to be removed from the kiln too late or too early. Ultimately, removing the wood too late or too early could result in reduced market value or a reduced quality in the final product, for instance furniture or home building products.

The first efforts to automate the process of measuring wood moisture content resulted in a meter that measured the conductivity of the core of the wood sample. Two pins would be tapped into the wood at opposite ends in the geometrical center of the sample. Electrical leads would be attached to the pins and connected to an ohmmeter, allowing the manufacturer to monitor the Resistance, R, of the sample's core. The manufacturer could thereby measure the Conductivity, $Y_R$, of the sample's core, and correlate that conductivity with wood moisture content.

The theory behind the conductivity concept is that the presence of moisture would increase conductivity of the core of the wood. As moisture in the core of the sample decreased during the drying process, conductivity would decrease until equilibrium moisture content was reached. This process has the potential to be successful in automating the process of measuring wood moisture content, but had one significant disadvantage.

The process of tapping pins into a wood sample still resulted in the destruction of a wood sample, making the sample unfit for use in wood products. In fact, before—when the manual process of measuring a wood sample was used—the sample would still have some residual (albeit reduced) value because it would be undamaged and could still be sold or used in the manufacturing of wood products. Using the conductivity process, the sample with the holes resulting from the pins would be damaged and would therefore have considerably less residual value.

The present invention eliminates the need to destroy a sample, making the process of measuring wood moisture content more economically efficient.

SUMMARY OF THE INVENTION

The object of the present invention is to measure the moisture content of wood in a noninvasive manner at the surface of a typical wood sample in a kiln. In addition, the invention will be able to endure the harsh environmental conditions of a wood kiln. The invention will measure wood moisture content in the range of six percent to fifty percent moisture content. The meter will be economical, sensible, and reliable.

The aforementioned objectives can be achieved by a device in a three-stage configuration. The first stage is a capacitor with two side-by-side plates. In this configuration, with the plates applied to the wood in the drying kiln, the wood functions as a dielectric. The combination of the wood and the plates is a standard circuit capacitor.

The second stage of the invention is a circuit incorporating the wood dielectric capacitor described in the first stage. The capacitor is integrated into a "one-shot" CMOS LM555 clock circuit. This circuit, when activated, creates a pulse width output proportional to the capacitance of the wood.

The third stage is a microprocessor database. The database correlates the capacitance of the wood in the drying kiln with the moisture content. This is accomplished by a look-up function, which equates the width of the output pulse (and thereby the capacitance of the wood) to the wood moisture content.

The result of this three-stage invention is that the wood moisture content can be measured by using an automated, noninvasive means. The invention improves the process of measuring wood moisture content by eliminating by reducing health hazards; by reducing the potential for human error; by improving efficiency; and by making wood-drying kilns more economically competitive.

DETAILED DECRIPTION OF THE INVENTION

The details of the invention will be described in the three aforementioned stages. Each figure described above will be referenced and explained in detail. Each facet of the invention and the supporting details will be related to the previously summarized descriptions.

Figure 1:
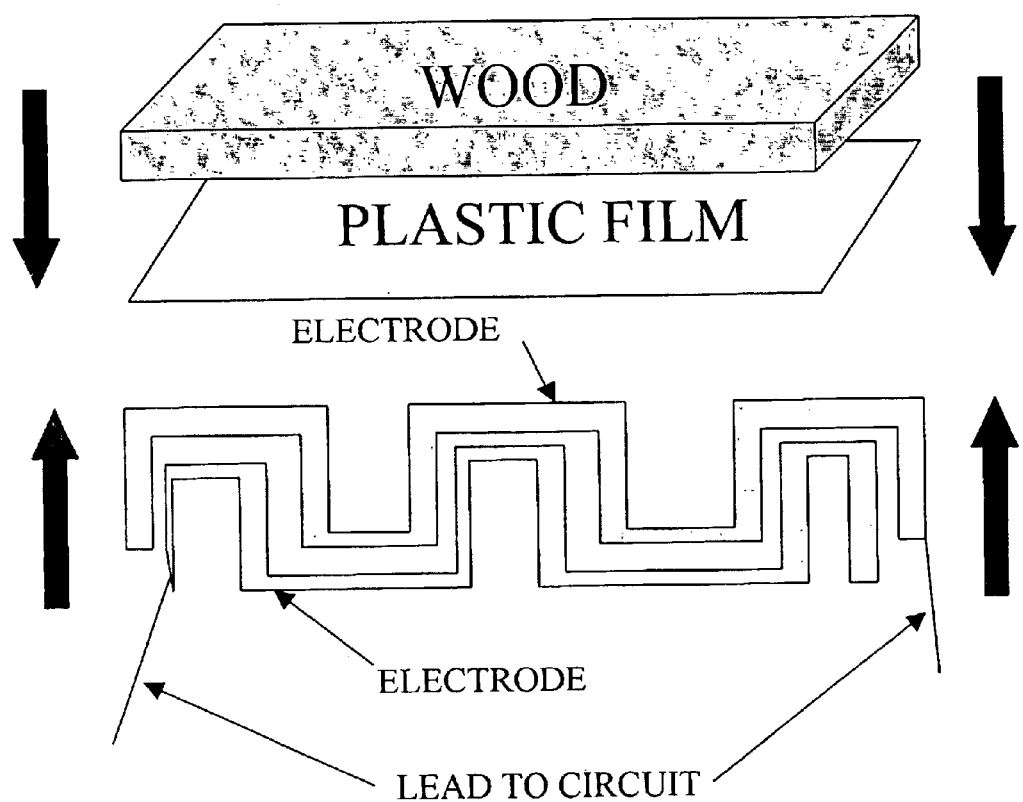
FIG. 1 is a cross-sectional view of the capacitor formed by the drying wood and the plates. Depicted are the "snake" style electrodes, encased in plastic, to be wedged between stacked lumber samples.

The first stage of the invention is in essence a parallel plate capacitor. Instead of the plates being parallel in the sense of opposite one another with the dielectric in the middle, they are parallel from one another's edges in contact with the dielectric and side-by-side. With the edges of the plates parallel, the wood between the plates still acts like a dielectric. See FIG. 1.

The plates are constructed of rigid aluminum (or other metal) sufficiently thin to fit between two boards and thick enough to resist being bent in the normal course of use. As long as the relationship between wood moisture and capacitance is established using the same sensor as is used to routinely to measure wood moisture content, the thickness of the aluminum is not material because it will be a constant (i.e., will not vary) and therefore will not impact the nature of the equations describing the nature of the relationship. For the sake of this invention, the thickness of the plates will be 5 mm.

The principle upon which Stage 1 based is most accurately described by the parallel plate capacitor equation, as described below:

$$C = (\in^* A)/\delta$$

where C=capacitance, $\in$=dielectric constant for wood, A=the surface area of the plates (or electrodes), and $\delta$=distance between plates. For the purposes of this invention, both A and $\delta$ are constant. The dielectric constant of wood, $\in_w$, will vary according to the amount of moisture in the wood sample being tested. Accordingly, the larger the moisture content in the wood, the larger the dielectric constant of the sample.

Of critical importance is the fact that the metal plates, which will hereinafter be called electrodes, are encased in a film of plastic. The plastic film on the electrodes mitigates the effect of "current" or "moisture" drift in the area between the electrodes by insulating the plates from the current drift and isolating the dielectric properties of the wood. Without the plastic film, current drift could result from high concentrations of surface moisture between the electrodes, effectively short-circuiting the intended path, which includes the dielectric properties of the wood itself.

Figure 2:
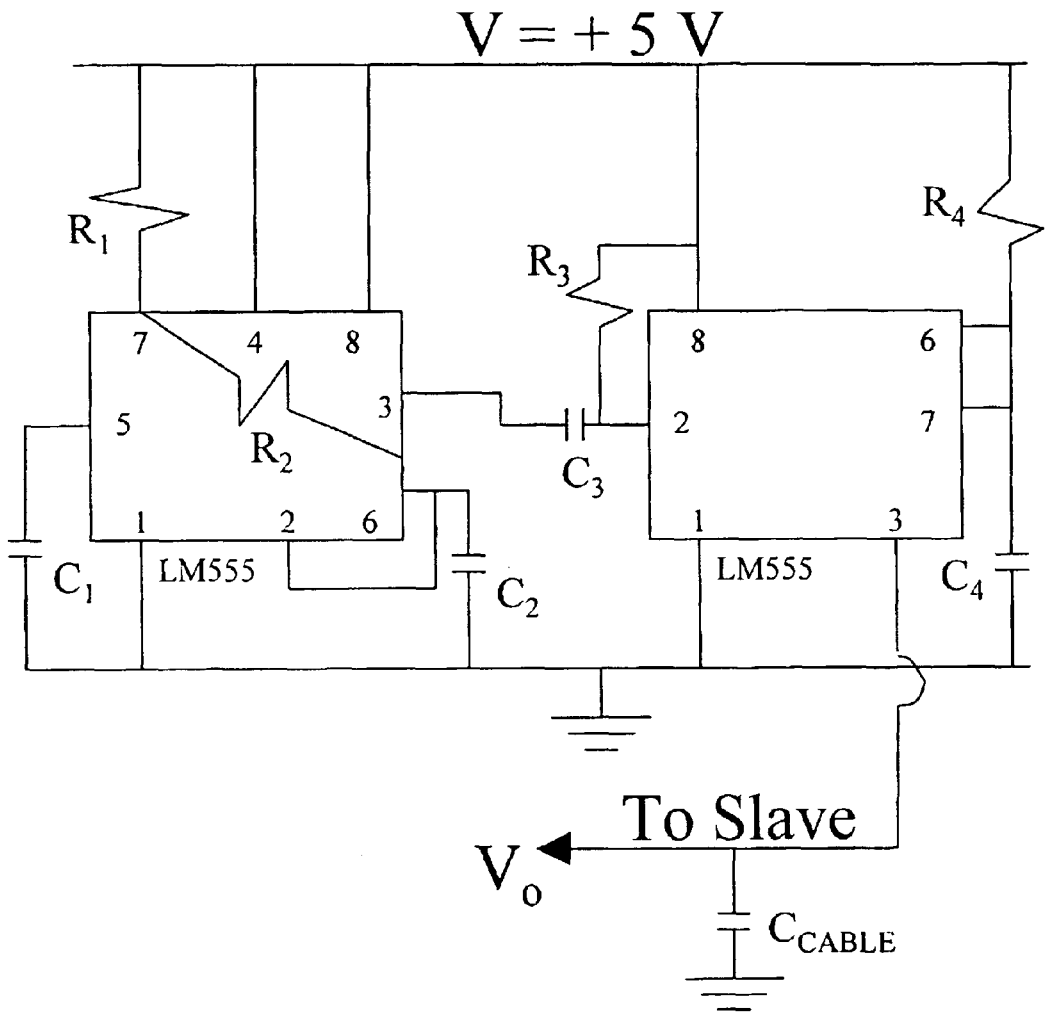
FIG. 2 is a schematic of the second-stage circuit.
Figure 3:
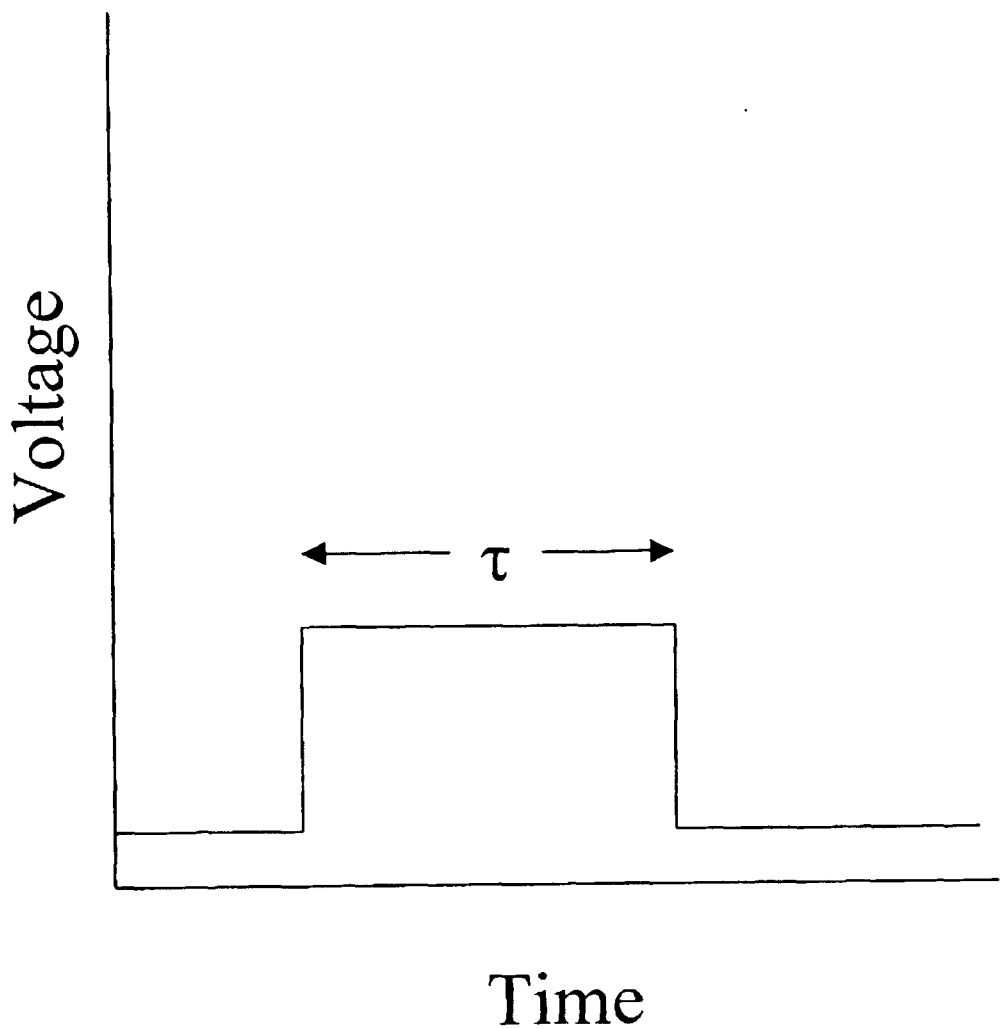
FIG. 3 is a drawing of a pulse width, described as $\tau$.

Stage 2 is a common clocking circuit. See FIG. 2. The circuit employs an LM555 CMOS chip in a "one-shot" fashion. A steady current is applied to the input of the circuit. The output of the circuit is a pulse with a length of $\tau$ in seconds, where $\tau$ is proportional to the capacitance of the wood. See FIG. 3 for a graphical depiction of pulse width, $\tau$.

Figure 4:
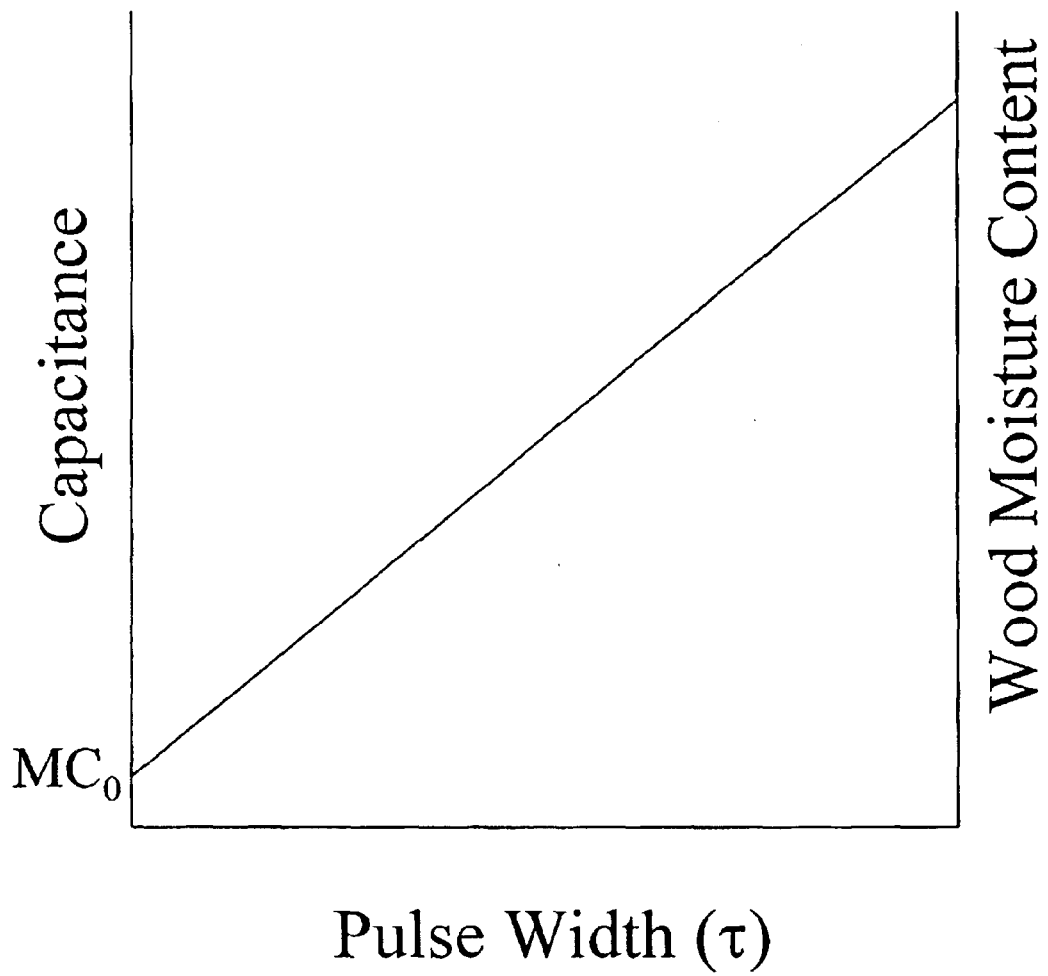
FIG. 4 is a graph describing the relationship between capacitance, C, and pulse width, $\tau$. The graph correlates wood moisture content and capacitance, the central premise of the invention.

Ultimately, the circuit converts the wood's capacitance, which varies based on a linear relationship dependent on moisture content, into a pulse length. The pulse length is measured by a microprocessor-based input register. The pulse length is then stored in the microprocessor as a digital value. A graphical depiction of the relationship between wood moisture content, capacitance, and pulse length that results from Stage 2 is shown in FIG. 4.

It is important to note that the circuit itself, including the leads from the power supply and to the microprocessor, will implicitly carry some latent capacitance $C_c$. For the purposes of this invention, the capacitance of the circuit will be minimal and constant. Cable capacitance will have no effect on the proportional relationship between the moisture content of the wood and the pulse length, as long as the length of the leads is kept constant.

CMOS integrated circuits are used due to their greater tolerance of high temperatures. By contrast, transistor-transistor logic (TTL) integrated circuits would likely encounter some minor disturbance at higher temperatures. As a result, TTL circuits are not suitable for this purpose.

Stage 3 of the invention is a microprocessor (standard PC) with accompanying ports for circuit inputs/outputs (such as an evaluation board). The function of Stage 3 is to measure the length of the output pulse, utilize a look-up function in a database, and correlate the pulse length to a prescheduled equivalent wood moisture content. The finished product is a constantly updated display that polls the database every five seconds for the current wood moisture constant and stores the values in a memory database for historical purposes.

The sequence of events in Stage 3 is described as follows:

1. A register in the microprocessor notes the time of arrival of the rising edge of the pulse, $T_1$, from Stage 2.
2. A second register in the microprocessor notes the time of arrival of the falling edge of the pulse, $T_2$, from Stage 2.
3. The microprocessor calculates the length of the pulse, $\tau$, by subtracting $T_1$ from $T_2$ ($T_2-T_1$).
4. The microprocessor calculates the moisture content using a look-up table.
5. The microprocessor displays the wood moisture content, as a percentage of volume, to the screen with a standardized refresh rate.

Figure 5:
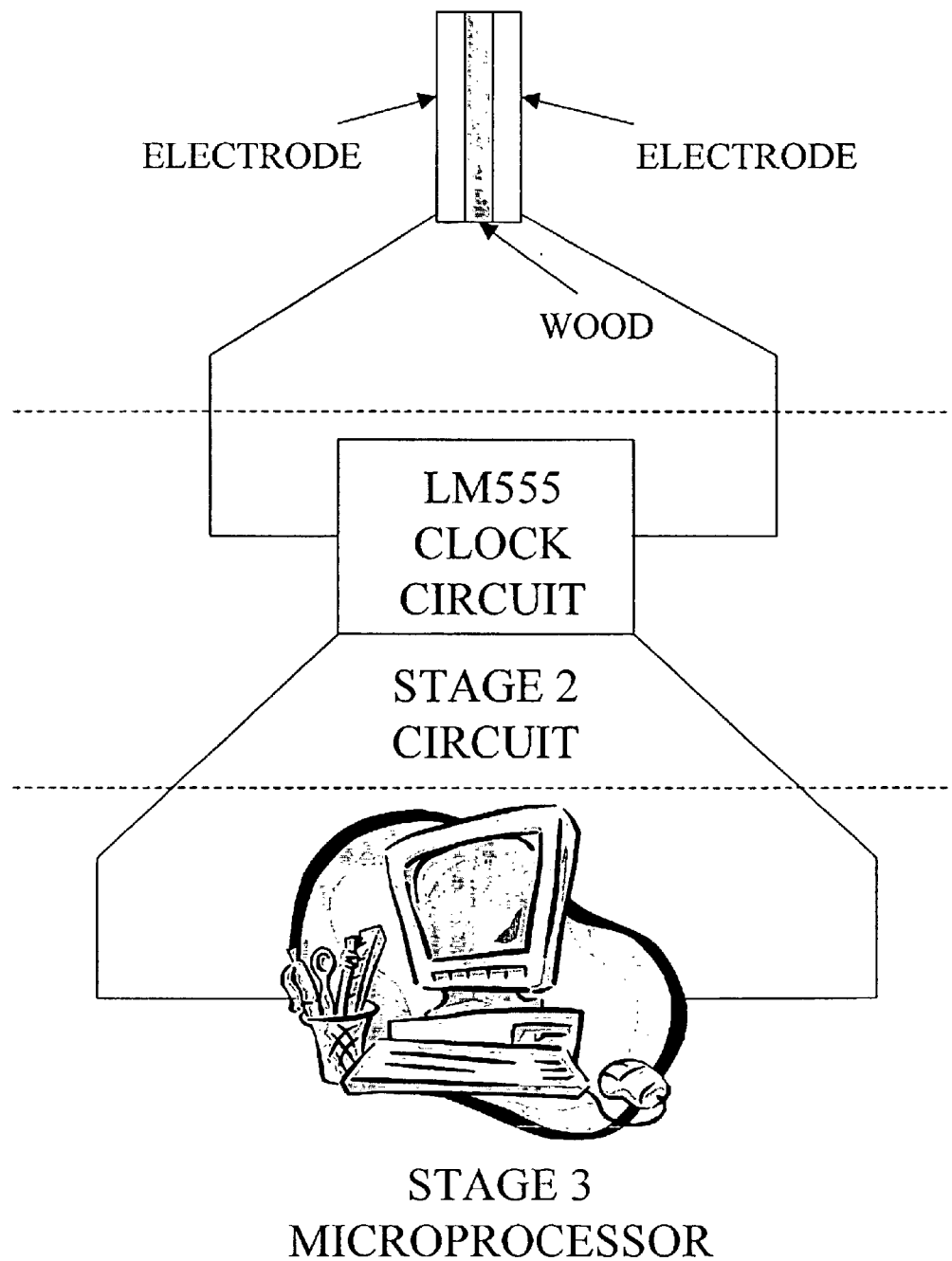
FIG. 5 is a drawing of the complete system.

The system as a whole is graphically depicted in FIG. 5.

We claim:

1. A method of measuring the moisture content of wood in a wood drying kiln utilizing a the principle that the dielectric properties of the wood are directly proportional to the amount of moisture in the wood, allowing for the measurement of wood moisture content in a three stage process:

a. Stage 1 being a pair of metal electrodes, encased in a plastic film, placed in direct contact with the wood to be measured and in a parallel fashion side by side;

b. Stage 2 being a clock circuit which produces an output voltage for a duration directly proportional to the capacitance and moisture content of the wood; and c. Stage 3 being a microprocessor which registers the time of the arrival of the rising edge of a clock circuit output voltage and the time of the arrival of the falling edge of a clock circuit output voltage, calculates the length of the clock circuit output voltage, and correlates the length of the wave output voltage with a corresponding wood moisture content value.

2. The method of claim 1 in which the principle that the dielectric constant of wood is variable with the moisture content of wood.

3. The method of claim 1 in which with the capacitance of the wood is proportional to the dielectric constant of the wood where capacitance, C, equals $(\in^* A)/\delta$; where $\in$ is the dielectric constant of a capacitor; where the surface area of the plates of a capacitor, A, and the distance between the plates of a capacitor, $\delta$, are held constant.

4. The method in claim 3 where the dielectric material in the capacitor is wood in a wood drying kiln in varies stages of drying.

5. The method in claim 1 where the moisture content of wood is obtained by creating a voltage pulse of a length which is directly proportional to the capacitance of the wood.

6. The method in claim 5 where the capacitance is directly proportional to the wood moisture content.

\* \* \* \* \*